United States Patent [19]

Hammerschmidt et al.

[11] Patent Number: 4,751,924
[45] Date of Patent: Jun. 21, 1988

[54] BALLOON CATHETER

[75] Inventors: Winrich Hammerschmidt, Hamburg-Schenefeld; Gerhard Zumbruch, Norderstedt, both of Fed. Rep. of Germany

[73] Assignee: NATEC, Institut fur naturwissen-schaftlichtechnische Dienste GmbH, Hamburg-Schenefeld, Fed. Rep. of Germany

[21] Appl. No.: 628,901

[22] Filed: Jul. 9, 1984

[30] Foreign Application Priority Data

Jul. 16, 1983 [DE] Fed. Rep. of Germany ....... 3325797
Feb. 3, 1984 [DE] Fed. Rep. of Germany ....... 3403681

[51] Int. Cl.⁴ ..................... A61M 16/00; A61M 29/00
[52] U.S. Cl. ................................ 128/207.15; 604/100; 604/101; 604/102; 604/103
[58] Field of Search ................... 128/207.15, 200.26; 604/96–103

[56] References Cited

U.S. PATENT DOCUMENTS

| 3,385,301 | 5/1968 | Harautuneian | 604/103 |
| 3,543,759 | 12/1970 | McWhorter | 604/100 |
| 3,731,691 | 5/1973 | Chen | 604/100 |
| 3,913,565 | 10/1975 | Kawahara | 128/207.15 |
| 4,020,849 | 5/1977 | Jackson | 128/207.15 |
| 4,119,099 | 10/1978 | Patel | 604/103 |
| 4,207,899 | 6/1980 | Patel | 604/103 |
| 4,222,384 | 9/1980 | Birtwell | 604/103 |

FOREIGN PATENT DOCUMENTS 425325 2/1976 United Kingdom ................ 604/103

Primary Examiner—Edward M. Coven
Assistant Examiner—K. M. Reichle
Attorney, Agent, or Firm—Roylance, Abrams, Berdo & Goodman

[57] ABSTRACT

The invention relates to a balloon catheter, particularly an endotracheal catheter, with a catheter tube of elastic, tissue-compatible material, in which the signal balloon (6) near the proximal end (3) of catheter tube (1) and the retention sleeve (4) near the distal end (2) of catheter tube (1) are present in a foil hose (15), extending over the entire length of the catheter tube, sheathing the catheter, and they are preformed in the hose in one piece. Foil hose (15) engages loosely on the catheter tube at the points of signal balloon (6) and retention sleeve (4), and is otherwise connected tightly with the catheter tube. Feed tube (5) connecting retention sleeve (4) with signal balloon (6) and the proximal end of the catheter tube can be formed by one or more grooves (14) in the outside wall of respirator tube (1), and the foil hose (15) covers the grooves to seal them gas- and liquid-tight from the outside.

Furthermore, the balloon catheter is provided with a special fitted connector, which is particularly simple and safe to handle.

19 Claims, 4 Drawing Sheets

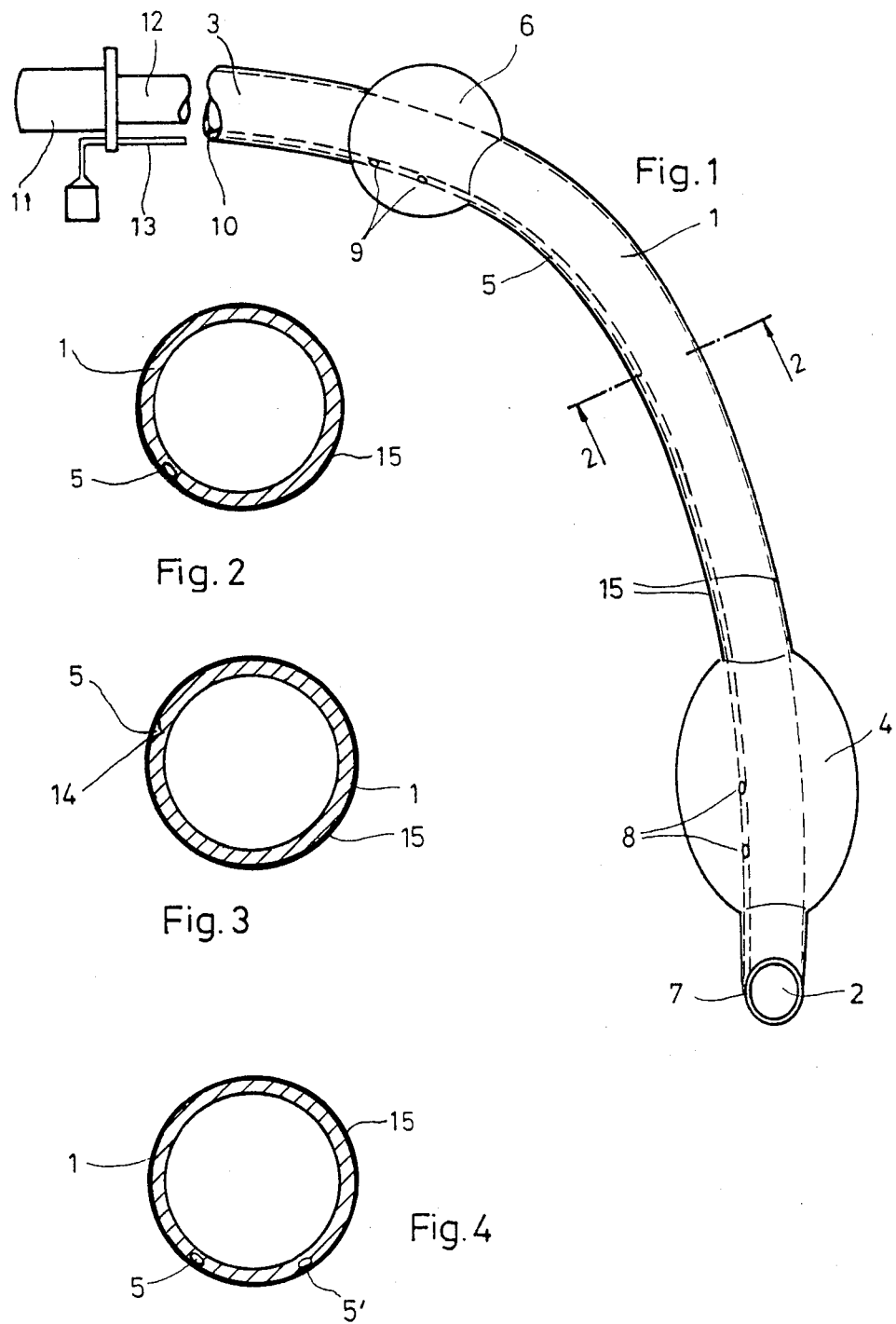

BALLOON CATHETER

BACKGROUND OF THE INVENTION

This invention relates to a balloon catheter, particularly in the form of an endotracheal catheter, with a catheter tube of elastic, tissue-compatible material, e.g., in the form of a respirator hose with a bevelled, open distal end and an open proximal end, and a connector, which is connected tightly with the catheter tube. The connector is optionally detachable.

Balloon catheters wherein a retention sleeve and a signal balloon are mounted on the catheter tube and are connected with each other through one or more feed tubes and with connection fittings for inflation of the retention sleeve and signal balloon are known in the art. German Pat. No. DE-OS 26 25 570 discloses a catheter with a sleeve balloon with is inflatable through an inflation lumen (channel), which is connected through the inflation lumen with a safety or signal balloon. The principle of the construction and the method of operation of this catheter are shown in FIGS. 1-4 of this patent. Both a sleeve balloon, in the vicinity of the distal end of the tube, and also a signal or safety balloon in the vicinity of the proximal end, are located on the catheter tube. As is shown particularly in FIG. 4, the air flow is fed through the feed lines in such a manner that the sleeve near the distal end is inflated first and the signal balloon is filled only when the pressure in the sleeve is greater than the predetermined standard inflation pressure. The safety balloon then lies beyond the sleeve balloon in the direction of air flow. This provides the advantage that no higher pressure is used during the safety balloon inflation than that in the sleeve balloon. However, this construction is very costly to manufacture and thus cannot be used in practice.

A catheter with inflatable sleeve and signal balloon is described in U.S. Pat. No. 3,543,759. In FIG. 1 of this patent, both balloons are arranged on the catheter tube and are connected with each other through a lumen 16 through the apertures 17 and 18, and with the side arm 25 which leads to the outside. The sleeve and signal balloons shown in FIGS. 1, 3, 4 and 6 of this patent are arranged separately on the catheter tube and connected tightly with the tube. This type of construction is quite costly.

Balloon catheters, e.g. as disclosed in German Pat. Nos. DE-AS 15 91 793, DE-OS 19 25 852, DE-AS 22 46 526, DE-AS 24 26 344, DE-OS 28 03 094 and DE-PS 30 28 568, are frequently used in surgery. For hygenic reasons, particularly to avoid infection in the hospital, i.e., the so-called hospital infection, each patient is treated more and more frequently with disposable new, sterile instruments. Hospitals are increasingly being forced to provide and use balloon catheters as sterile instruments which are intended to be used only once.

However, until the present time, the customary types of structures of balloon catheters intended for only one use have been very costly. An endotracheal catheter of the most useful type of structure, for example, with a retention sleeve, is essentially composed of six different individual parts, including a respirator tube, a retention sleeve, a signal balloon, a ventilation tube as a connection between the sleeve and signal balloon, a connector and connection fittings with shoulders on the signal balloon for a retention injector. Other balloon catheters are constructed in a similar manner. The parts must be manufactured individually and then assembled and, if necessary, are connected tightly or permanently with each other. Their manufacture is therefore very time consuming and burdensome.

Therefore, a need exists for balloon catheters, particularly endotracheal catheters, which can be manufactured so that the manufacturing costs of such instruments, which are to be used only once, are commercially feasible.

Therefore, the object of the present invention is to provide balloon catheters, particularly endotracheal catheters which are characterized by considerably simpler and more advantageous construction than customary balloon catheters, with sleeves and signal balloons, which can be manufactured at low cost.

BRIEF DESCRIPTION OF THE DRAWINGS

FIG. 1 is a side view of an embodiment of an endotracheal catheter with a connector according to this invention.

FIG. 2 is a transverse cross section taken along line 2—2 of FIG. 1.

FIG. 3 is a transverse cross section through another embodiment of an endotracheal catheter, in which the catheter tube has a groove on the outside wall which is covered by a sheathing foil hose.

FIG. 4 is a transverse cross section of another configuration of an endotracheal catheter according to this invention, with two feed tubes in the wall of the sheathed catheter tube.

BRIEF DESCRIPTION OF THE INVENTION

Figure 5:
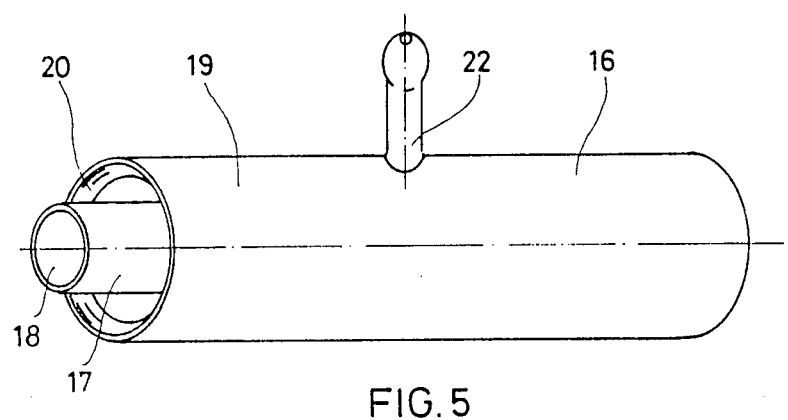
FIG. 5 is a perspective view of one embodiment of the connector according to this invention.

According to this invention, there is provided a balloon catheter, particularly an endotracheal catheter, with a catheter tube 1 of elastic tissue-compatible material, having a bevelled, open distal end 2 and an open proximal end 3. The device includes a connector 11, which is detachably or permanently connected with catheter tube 1. An inflatable retention sleeve 4 is provided on the catheter tube 1 in the vicinity of the distal end 2, connected tightly with the tube. An inflatable signal balloon 6 is located on the tube 1 in the vicinity of the proximal tube end 3, connected tightly with the tube. At least one feed tube 5 is provided connecting retention sleeve 4 with signal balloon 6. There is also provided a connection fitting with a shoulder for a retention injector. Tube 5 is tightly closed off at distal tube end 2. Catheter tube 1 is sheathed over its entire length on the outside by a thin foil hose 15. This foil hose 15 engages loosely in the areas provided for retention sleeve 4 and signal balloon 6 on the outside wall of catheter tube 1 and is flared in such a manner at these points that it can be inflated at these points through one or more feed lines 5 with feed tube openings 8 and 9 into retention sleeve 4 and signal balloon 6, respectively. The hose 15 is connected tightly to the tube 1 in the other areas. Feed tube or tubes 5 which extend over the entire length of the catheter tube 1 open at the proximal end 3 into a connection opening 10 or several connection openings 10. The connector 11 has a connection fitting 12 and is provided with a shoulder. The connector 11 also has one or more connection elements to connect with connection opening or openings 10.

An advantage of the balloon catheter of this invention resides in that it is composed of only a few separate parts, including the catheter tube with sheathing foil hose, in which the retention sleeve and signal balloon are already preshaped. Also, the connector is advantageously adapted to the shape of the balloon catheter according to this invention, with connection elements for connection with the feed tube or tubes. For low cost manufacture of the balloon catheter according to this invention, it is essential that the retention sleeve and signal balloon be constructed as thin, inflatable parts of a foil hose which can be pulled over the catheter tube. If necessary, the foil hose can be manufactured simultaneously with and in the same manner as the catheter tube in such a manner that the tube is tightly sheathed.

The catheter tube can be extruded in a known manner as a simple hose and sheathed thereafter with the foil hose. Base and sheathing hoses can both consist of polyvinylchloride resin of 80 A Shore hardness and can be connected with each other during the sheathing by heat welding, sealing, cementing and/or tight and gas and liquid-tight shrink-fitting. Only the areas which are provided for the retention sleeve and signal balloon do not adhere to each other, and no welding, sealing or special permanent connection occurs at these points. As a result of this, the foil hose engages only loosely on the catheter tube in these areas. If desired, the foil hose can also be formed out into a blister of desired shape and size, in the areas provided for the formation of the retention sleeve and signal balloon. A suitable release compound for this purpose, e.g., a vinyl chloride-vinyl acetate copolymer, in which the vinyl acetate is partially saponified, is applied on the surface of the base hose before the sheathing, where the retention sleeve and signal balloon are later to be located. No tight adherence occurs between the base hose and the foil hose, as a result of the treatment with the release agent during the sheathing.

The release agent can be applied with pressure or by a spraying device. The base hose must be heated before application of the release agent, and/or thereafter, so that the foil hose adheres well to the base hose.

The manufacture is thus greatly simplified and the balloon catheter according to this invention can be manufactured in assembly-line fashion, in which the sheathed catheter tube is produced continuously as an endless tube, e.g., by extrusion processes, and can be sectioned at certain points. The mass production which is thus made possible allows much more rapid manufacture of the balloon catheter of this invention in large quantities, so that the price per individual unit can be set sufficiently low that it is economically advantageous.

The retention sleeve and signal balloon are fastened permanently and gas and liquid tight to the catheter tube and are connected through one more openings with the feed tube, whereby it can be blown out or ventilated.

The foil hose with preformed sleeve and balloon can be tightly connected with the catheter tube by suitable means. To accomplish this, proper selection of the material of the parts which are to be connected is important. Since both tube and the foil hose are generally rubber, particularly soft rubber, or a synthetic polymer, such as polyvinylchloride, high-pressure polyethylene or a thermoplastic polyurethane, or a highly polymerized or high molecular elastic organo silicone composition, such as Silastic ®, they are preferably cemented together, or sealed or welded and/or connected by shrink-fitting of the foil hose with the catheter tube at the points provided for that purpose.

This invention also relates to a connector adapted to the requirements of the balloon catheter, either connected permanently or detachably with the balloon catheter.

Connectors or connection fittings with shoulders are needed to provide tight but detachable connections between tubes or hoses of the same or different diameters, for example, for the connection of a catheter tube with the feed tube of a respirator or a narcosis apparatus. Such connectors are widely used in medical technology and in principle consist of two tube elements connected tightly with each other, which are often tapered conically toward the ends and of which the diameters are adapted to the diameters of the tubes or hoses to be connected.

In the balloon catheter according to this invention, both the catheter tube and also the feed tube or plurality of feed tubes connected with the signal balloon and the retention sleeve are open at the proximal end. The connector therefore must be so configured that it simultaneously provides both the connection of the catheter tube with the desired medical apparatus, e.g., a respiratory, narcosis or suction/drainage apparatus, and also the connection of the feed tube with a suitable air supply, e.g., an air jet, providing the desired volume of air, or an air pump, e.g., a retention injector. This is attained in a configuration of the balloon catheter of this invention wherein the catheter is provided with a connector which has connection elements for connection to one or more connection openings of the feed tube in the form of connection fittings, adjacent to a connection fitting for the proximal end of the catheter tube. The number and arrangement of the connection fittings correspond to the number and arrangement of the connection openings at the proximal end of the catheter tube.

Figure 6:
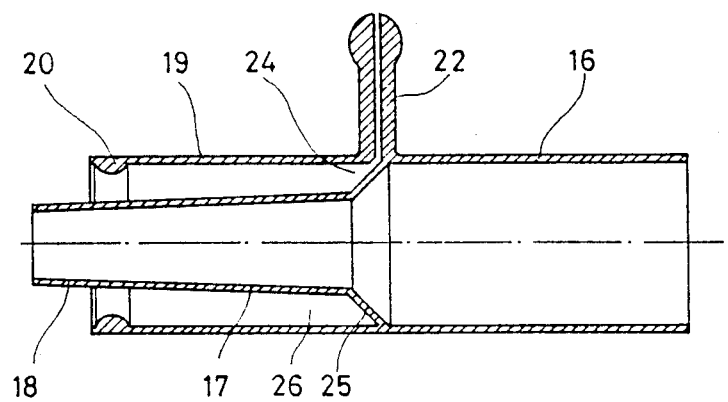
FIG. 6 is a diagrammatical longitudinal cross section through the preferred embodiment of the connector according to the invention shown in FIG. 5.

In an especially preferred embodiment of this invention, as shown in FIGS. 5 and 6, the balloon catheter is provided with a connector which has a wide tube fitting 16 and a narrow tube fitting 17. The passage from wide tube fitting 16 to narrow tube fitting 17 is formed through a conical tubular element 25, and includes a wide tube which is arranged concentrically around narrow tube fitting 17 and is provided with a connecting tube element 22 to an air feed line. Connecting tube element 22 is connected through an annular passage 24 with the hollow cylindrical chamber 26 which is formed between the inside wall of wide tube 19 and the outside wall of narrow tube fitting 17. The distance between the inside wall of wide tube 19 and the outside wall of narrow tube fitting 17 is so adapted to the wall thickness of the catheter tube 1 which is to be inserted as to obtain a gas-tight connection.

This advantageous construction permits the connector to be connected rapidly and without problem with the balloon catheter. The connector has the special advantage that it fits on the catheter tube in any desired position, with the feed tube in the wall and coming out of the wall at the end of the catheter tube, so that no canting, tilting or erroneous insertion to the side can occur. If the proximal end of the catheter is pushed open over the end of the narrow tube fitting until the pushed down catheter tube forms a gas seal between the wide tube and the narrow tube fitting, then a sealed hollow cylindrical air chamber is formed between the end of the pushed-open catheter tube and the air inlet of the feed line coming through the connecting tube element into the hollow cylinder chamber. With desired positioning of the connector on the catheter tube, the air in this chamber can easily get into the feed tube or tubes found in the wall of the catheter tube. The safety in handling the connector is thus greatly increased.

DETAILED DESCRIPTION OF THE INVENTION

The endotracheal catheter shown in FIG. 1 consists of a catheter tube 1 of elastic, tissue-compatible material with a bevelled and rounded open distal end 2, which can be inserted into the trachea of a patient, and an open proximal end 3, which can be connected with a respiratory or narcosis apparatus through a connector 11 fitted with connection fittings 12 and 13. The connector 11 includes a shoulder. Near the distal end 2 and spaced therefrom is located an inflatable retention sleeve 4 connected permanently and gas- and liquid-tight with catheter tube 1.

Near the proximal end 3 of tube 1 and spaced therefrom is located an inflatable signal balloon 6, which is a hollow cylinder surrounding catheter tube 1 to which it is connected permanently and gas- and liquid-tight.

In the wall or on the outside of the wall of catheter tube 1, as shown in FIG. 1, a feed tube 5 extends over the entire length of tube 1, with a connection opening 10 at the proximal end of tube 1, which can be connected with a connection fitting 13 provided with a shoulder. Feed tube 5 serves for inflation and ventilation or release of retention sleeve 4 and signal balloon 6. Therefore, it is connected with both devices through one or more openings 8 and 9 in the areas of retention sleeve 4 and signal balloon 6. Feed tube 5 is connected gas- and liquid-tight at the distal end 2 of tube 1.

The shape and size of retention sleeve 4 and signal balloon 6 may be other than the shapes and sizes shown in FIG. 1. Retention sleeve 4 is generally of elongated shape and is generally larger than signal balloon 6.

Instead of one feed tube 5, as shown in FIG. 1, two, three, four or six feed tubes may be provided in or on the wall of catheter tube 1. Providing a plurality of tubes has the advantage that air can be exchanged more rapidly between the sleeve and balloon, and, therefore, the sleeve and balloon can be more rapidly inflated and deflated. A catheter tube 1 is shown in cross section in FIG. 2 with one feed tube 5. In FIG. 4, a corresponding catheter tube 1 is shown in cross section with two feed tubes 5 and 5′. The feed tubes may be in any desired position relative to each other.

In all of the embodiments of this invention, catheter tube 1 is sheathed on the outside firmly and tightly over its entire length with a thin foil hose or covering 15. This foil hose 15 loosely engages on the outside wall of catheter tube 1 at the points 4 and 6, and can be inflated at these points through one or more feed lines 5 with feed line openings 8 and 9 to provide retention sleeve 4 and signal balloon 6.

In another preferred embodiment of this invention shown in FIG. 3, one or more grooves 14 can be provided in the outside wall of catheter tube 1. The foil hose 15 tightly and firmly sheaths catheter tube 1, thus forming one or more feed tubes 5. The groove is free within the areas of retention sleeve 4 and signal balloon 6, so that the air flowing through feed tube 5 can enter and fill sleeve 4 and balloon 6 without obstruction. This embodiment, in which retention sleeve 4 and signal balloon 6 are configured in one piece as thin, flared parts of the foil hose 15, which engages tightly on the outside wall of catheter tube 1, and wherein one or more feed tubes 5 are formed by grooves 14 in the outside wall of catheter tube 1 and by the sheathing foil hose 15, offers special functional advantages.

The foil hose, in which the retention sleeve and signal balloon are preformed, can consist of a suitable elastic and thermoplastic material, e.g., polyethylene, polyvinylchloride, latex or thermoplastic polyurethane.

Proximal end 3 of the endotracheal catheter is provided with a suitably fitted connector 11. In FIG. 1, connector 11 can be provided with one connection fitting 12 with a shoulder for catheter tube 1 and, corresponding to the number of feed tubes 5 in or on the wall of tube 1, with a corresponding number of connection fittings 13 with shoulders for the proximal connection openings 10 of feed tubes 5.

Especially preferred embodiments of the connector according to this invention are shown in FIGS. 5–11. FIGS. 5 and 6 show the connector consisting of a wide tube fitting 16, a connecting tube element 22 for the air feed line, the outside continuation of the wide tube fitting 16, indicated as wide pipe 19, and a narrow tube fitting 17, which is arranged concentrically within wide tube 19.

The specific construction of the connector according to this embodiment of the invention is shown in detail in FIG. 6. Wide tube fitting 16 serves for connection to the medical apparatus, e.g., a respiratory, narcosis or suction/drainage apparatus, while narrow tube fitting 17 is provided for connection to the proximal end of the catheter tube. Wide tube fitting 16 progresses in the middle of the connector into a conically tapering tube element 25, to which narrow tube fitting 17 is directly connected. Wide tube 19 is provided with connecting tube element 22, to which an air feed line can be attached, and which is connected with the hollow cylindrical chamber 26 through an annular passage 24.

When the proximal end of catheter tube 1 is inserted into hollow cylindrical chamber 26 between the inside wall of wide tube 19 and the outside wall of narrow tube fitting 17, and is pushed open on tube fitting 17, then, as a result of the adaptation of the space between the inside wall of wide tube 19 and the outside wall of narrow tube fitting 17 on the wall thickness of the catheter tube, a gas-tight seal of the inserted catheter tube from the outside air is formed. The average distance between the inside wall and the outside wall is preferably identical to the wall thickness of the inserted catheter tube, but slight deviations from the wall thickness can be tolerated.

In order that the inserted proximal end of the catheter tube blocks off the hollow cylindrical chamber 26 from the outside air, the air flow coming through connecting tube element 22 and annular passage 24 into hollow cylindrical chamber 26 can only get through the one or more connection openings in the end of the catheter tube into the air feed tube in the wall of the catheter tube, from whence the air flows into the signal balloon and the retention sleeve, which are thus inflated.

With the construction of the connector according to this invention, it makes no difference in what position the catheter tube is connected with the connector, because a connection between the connection openings of the air feed tube in the end of the catheter tube and the air flow into the hollow cylindrical chamber 26 exists in any desired setting.

In order to facilitate the telescoping of the catheter tube on the tube fitting 17 and to guarantee a tight seat on the tube fitting, narrow tube fitting 17 is conically tapered in the direction of end 18.

Likewise, wide tube fitting 16 is preferably configured conically widened toward the middle of the connector, whereupon a tighter and more permanent seat of the connection tube for medical apparatus is achieved.

Open end 18 of narrow tube fitting 17 can terminate in a plane with the end of wide tube 19; it can also lie within wide tube 19; but preferably it projects out over the end of wide tube 19.

In another preferred embodiment of the connector of this invention, the open end of wide tube 19 is provided with an annular inside bead 20. This permits the rapid, permanent and gas-tight mounting of the proximal end of the catheter tube on narrow tube fitting 17 and results in improved operation of the connector. Thus, the catheter tube which is pushed open is pressed tightly on the outside wall of narrow tube fitting 17 by the bead 20 and sealing from the outside of the connection of catheter tube and connector is obtained.

Figure 9:
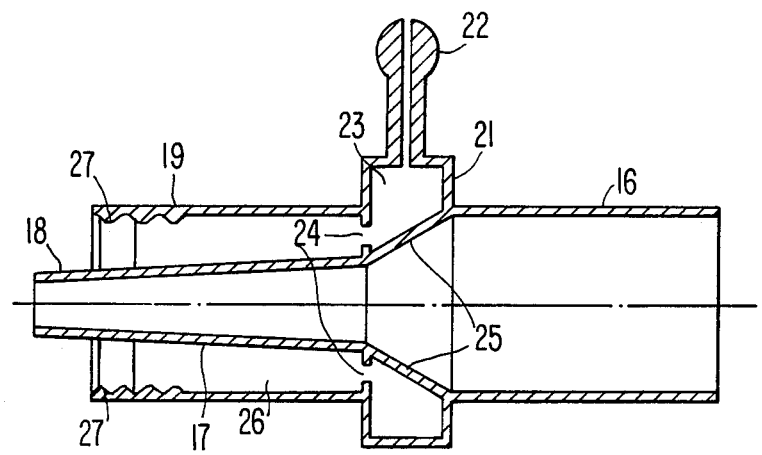
FIG. 9 is a diagrammatical longitudinal cross section of another embodiment of the connector.

In yet another embodiment, the open end 19 of the catheter tube is provided with annular inside threads 27 (see FIG. 9). These threads 27 engage the outer surface of the proximal end of the tube.

Other possibilities of permanent and gas-tight connection of catheter tube and connector, such as gluing or cementing or welding, are likewise possible with suitable selection of catheter tube and connector materials, and are mainly to be considered for products to be used only once. Furthermore, particularly when the connector is provided to be used only once and is manufactured on a suitable plastic material, preferably by an injection molding process, further advantageous embodiments of a connector according to the invention are obtained by modification of connecting tube element 22. This generally serves for the attachment of a flexible connection fitting for air feed or for retention injector, e.g., a Luer injector. For this purpose, the connector according to this invention is preferably provided with a connecting tube element 22 with a funnel shaped opening 29 (see FIG. 11) adapted to a retention injector.

Figure 10:
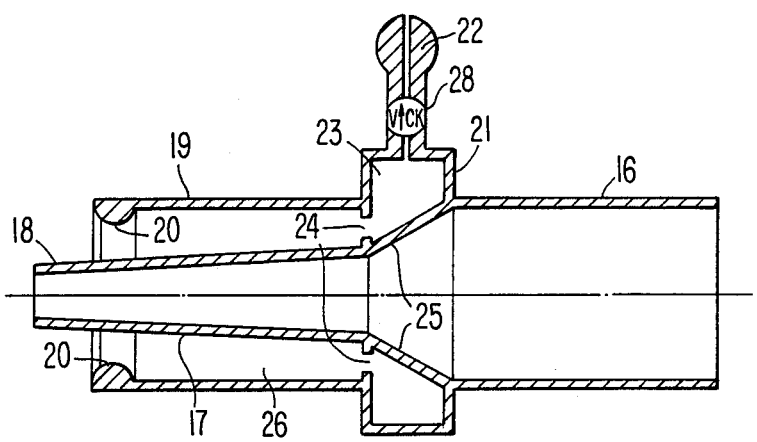
FIG. 10 is a diagrammatical longitudinal cross section of yet another embodiment of the connector.
Figure 11:
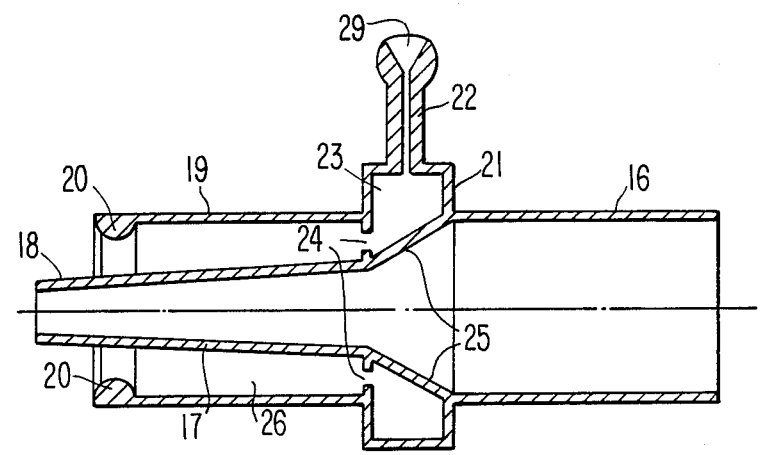
FIG. 11 is a diagrammatical longitudinal cross section of a further embodiment of the connector.

In another preferred embodiment, the connection tube element 22 is provided with a check valve 28 (see FIG. 10). This guarantees that the dosed air volume required for a certain inside pressure in the retention sleeve remains in the system, and cannot penetrate through connecting tube element 22.

Finally, in another advantageous configuration of the connector according to this invention, a gripping bead or one or more gripping strips can be provided on the outside wall of wide tube 19, approximately at the level of connecting tube element 22, further improving the manipulability of the connector.

Figure 7:
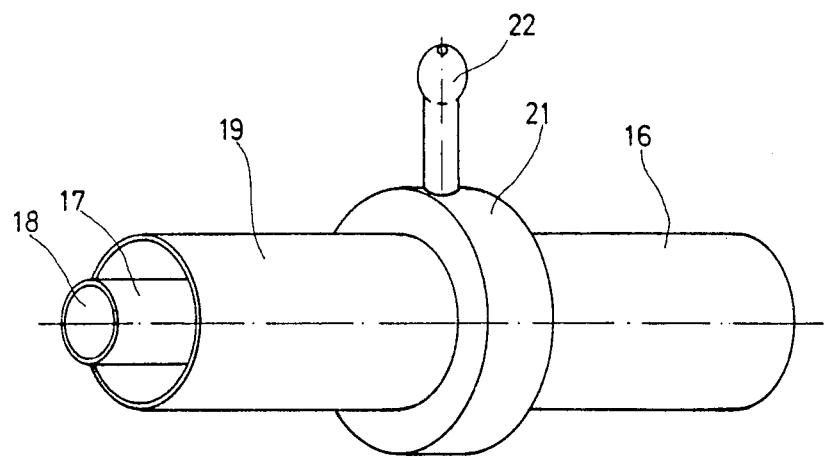
FIG. 7 is a perspective view of another embodiment of the connector.
Figure 8:
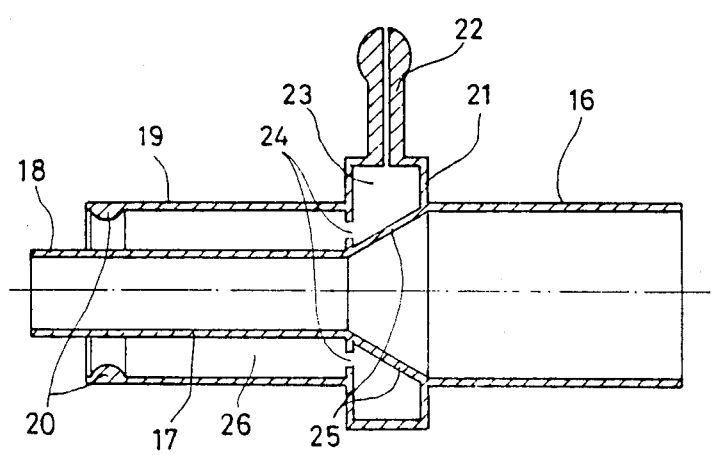
FIG. 8 is a diagrammatical longitudinal cross section through the embodiment of the connector shown in FIG. 7.

FIGS. 7 and 8 show other embodiments of the connector according to this invention, which are particularly useful for manufacture of the connector of certain metals, e.g., V2A steel. According to this embodiment, the connector consists of a wide tube fitting 16, a conically tapered tube element 25 and a narrow tube fitting 17, as well as a wide tube 19 surrounding narrow tube fitting 17 concentrically, with inside border bead 20 at the end of wide tube 19. Connecting tube element 22 for the air feed line, is located in an annular member 21 which is situated in the middle of the connector, over conically tapering member 25.

Annular member 21 can be solid but is preferably hollow. If it is solid, it contains a tube or bore not shown in the drawings which forms the connection for the air flow from connecting tube element 22 to hollow cylindrical chamber 26. Annular member 21 as shown in FIG. 8 is hollow, so that air can flow through connecting tube element 22 into annular hollow chamber 23 and can be discharged through one or more passages 24 and flow into hollow cylindrical chamber 26. FIG. 8 shows that annular member 25 thus includes an annular hollow chamber 23, which is connected directly with connecting tube element 22 and through one or more openings or an annular passage 24 with hollow cylindrical chamber 26.

The connector according to this embodiment of the invention can be manufactured of any material which meets the special requirements for medical apparatuses and particularly for a medical catheter. The material particularly must be sterilizable. The selection of suitable material also depends on the intended length of use of the connector. A durable material must be used if the article is to be used repeatedly, e.g., suitable metal such as V2A steel. However, for one-time use, less costly materials, such as plastics, e.g., polyolefins, particularly polyethylene, polyethylene vinylacetate (EVA), polyvinylchloride, polystyrene, and copolymers such as SBS and ABS and even thermoplastic polyurethanes, can be used.

It is understood that balloon catheters according to this invention are provided particularly for endotracheal catheters, but that because of their universal construction, they can also be used in various modified forms for other purposes, e.g., advantageously as heart and lung catheters or stomach probes.

Furthermore, the balloon catheter according to this invention can be provided with a low pressure sleeve and a high pressure sleeve.

What is claimed is:

1. A balloon catheter comprising:
    an elastic, tissue-compatible catheter tube having an open distal end and an open proximal end, said tube being of uniform material and of one-piece construction;
    an inflatable retention sleeve and an inflatable signal balloon located on said tube, said retention sleeve being located near said distal end, said signal balloon being located near said proximal end;
    said tube having a longitudinal groove in the exterior surface thereof, said groove extending from the proximal end to said signal balloon, to said retention sleeve;
    a thin foil hose which completely sheathes said tube, said foil hose being of one-piece construction and of uniform material, said groove of said tube and said foil hose forming a feed line extending from the proximal end to said signal balloon to said retention sleeve;
    said retention sleeve and said signal balloon being formed by said tube and said foil hose; and a connector which connects to said proximal end, said connector having an element which connects with said feed line and a narrow fitting which engages said tube.

2. A catheter as defined in claim 1 wherein said foil hose is in tight contact with said tube at all points of the exterior surface of said tube except at said groove, said retention sleeve and said signal balloon.

3. A catheter as defined in claim 1 wherein said foil hose is connected with said tube at all points of the exterior surface of said tube except at said groove, said retention sleeve and said signal balloon.

4. A catheter as defined in claim 1 wherein said connector further comprises a wide tubular fitting and a conical portion, said conical portion connecting said wide tubular fitting with said narrow fitting to form a continuous passageway;

said connector further comprises a wide tubular portion concentrically positioned around said narrow fitting such that a chamber is formed between said wide tubular portion and said narrow fitting;

said proximal end of said tube being received within said chamber.

5. A catheter as defined in claim 4 wherein said narrow fitting extends out of said wide tubular portion.

6. A catheter as defined in claim 4 wherein said wide tubular portion has an open end and an annular bead projecting inwardly at said open end.

7. A catheter as defined in claim 4 wherein said wide tubular portion has an open end and a thread projecting inwardly at said open end.

8. A catheter as defined in claim 4 wherein said connector includes an air feed line extending from the exterior of the connector to said chamber; said chamber having a portion with a height approximately equal to the thickness of the wall of said tube such that when said tube is inserted within said connector, said chamber is air-tight.

9. A catheter as defined in claim 8 wherein said connector includes a check valve assembly in said air feed line.

10. A catheter as defined in claim 8 wherein said air feed line includes a funnel-shaped portion forming the inlet of said air feed line in said connector.

11. A catheter as defined in claim 8 wherein said connector includes a ring portion having a diameter greater than said wide tubular fitting, said ring portion being adjacent said conical portion and forming an annular chamber with said conical portion, said annular chamber being in communication with said chamber and said air feed line extending out said ring portion such that a continuous passageway is formed by said chamber, said annular chamber and said air feed line.

12. A catheter as defined in claim 11 wherein said ring portion is hollow and is connected by a passageway to said chamber.

13. A catheter as defined in claim 8 wherein said narrow fitting has a first end connected to said tubular portion and a second end opposite said first end, said fitting tapering from said first end to said second end.

14. A catheter as defined in claim 1 wherein said connector is detechable from said tube.

15. A catheter as defined in claim 1 wherein said foil hose is flared out in the areas of said retention sleeve and said signal balloon.

16. A catheter as defined in claim 1 wherein said retention sleeve and said signal balloon inflate at the same rate.

17. A catheter as defined in claim 1 wherein said connector includes an inner and an outer tube, said inner tube comprising said narrow fitting, said inner tube forming a continuous passageway with said catheter tube;

said inner and said outer tube being concentric and forming a chamber therebetween, said tubes comprising in part said element, said chamber being in communication with said feed line.

18. A catheter as defined in claim 17 wherein said inner and outer tubes are concentric.

19. A balloon catheter comprising:

an elastic, tissue-compatible catheter tube having an open distal end and an open proximal end, said tube being of uniform material and of one-piece construction;

an inflatable retention sleeve and an inflatable signal balloon located on said tube, said retention sleeve being located near said distal end, said signal balloon being located near said proximal end;

said catheter tube having a feed line therein extending from said proximal end to said signal balloon, to said retention sleeve;

a thin foil hose which completely sheathes said tube, said foil hose being of one-piece construction and of uniform material;

said foil hose being tightly in abutment with the exterior of said tube at all locations excepts at said retention sleeve and said signal balloon, said foil hose being loose about said catheter tube at said retention sleeve and said signal balloon such that said sleeve and said balloon are formed by said foil hose and said tube.

* * * * *